United States Patent [19]

Bach et al.

[11] Patent Number: 4,795,727

[45] Date of Patent: Jan. 3, 1989

[54] RHODIUM CATALYSTS AND METHODS OF PREPARATION AND USE THEREOF

[75] Inventors: Hanswilhelm Bach, Duisburg; Helmut Bahrmann, Hamminkeln-Brünen; Boy Cornils, Hofheim; Werner Konkol; Ernst Wiebus, both of Oberhausen, all of Fed. Rep. of Germany

[73] Assignee: Ruhrchemie Aktiengesellschaft, Fed. Rep. of Germany

[21] Appl. No.: 47,663

[22] Filed: May 8, 1987

[30] Foreign Application Priority Data

May 13, 1986 [DE] Fed. Rep. of Germany ....... 3616057

[51] Int. Cl.$^4$ .............................................. B01J 31/22
[52] U.S. Cl. ..................... 502/161; 502/166; 568/454
[58] Field of Search ................................. 502/161, 166

[56] References Cited

U.S. PATENT DOCUMENTS

| Re. 31,812 | 1/1985 | Kuntz | 502/166 X |
| 3,937,742 | 2/1976 | Yoo | 502/161 X |
| 4,142,992 | 3/1979 | Knowles et al. | 502/166 |
| 4,197,253 | 4/1980 | Kaplan | 502/161 X |
| 4,578,523 | 3/1986 | Bahrmann et al. | 502/166 X |

FOREIGN PATENT DOCUMENTS 2478078 9/1981 France ................... 502/166

*Primary Examiner*—Patrick P. Garvin
*Attorney, Agent, or Firm*—Jordan B. Bierman

[57] ABSTRACT

A process for the preparation of a rhodium catalyst comprising dissolving a carboxylic acid salt of rhodium in a solvent taken from the class consisting of aliphatic, cycloaliphatic, aromatic hydrocarbons and mixtures thereof. The carboxylic acid has 2 to 18 carbon atoms. This salt is reacted with carbon monoxide and hydrogen to form a rhodium hydridrocarbonyl which is reacted with an aqueous solution of a triaryl phosphine. The aqueous solution may be present during the initial reaction of the rhodium salt or may be added thereafter. A catalyst which is the product of the foregoing process is also disclosed, as is a method of producing aldehydes using the catalyst.

10 Claims, No Drawings

RHODIUM CATALYSTS AND METHODS OF PREPARATION AND USE THEREOF

The present invention relates to an improved process for the preparation of aldehydes by the reaction of olefinically unsaturated compounds in an aqueous medium and in the presence of water soluble rhodium complex compounds as catalysts. The aim of the new procedure is, by preforming the catalyst, to shorten the reaction period in the initial phase of the reaction and to minimize the loss of valuable metal in this reaction step.

The preparation of aldehydes and alcohols by the reaction of olefins with carbon monoxide and hydrogen is known. The reaction is catalyzed with hydridometal carbonyls, in particular of metals Group VIII of the Periodic Table. While the classical process in its various technical embodiments uses cobalt catalysts, recently rhodium catalysts have been gaining more and more in significance. In contrast to cobalt, rhodium permits the reaction to be carried out at low pressure; moreover, straight-chain n-aldehydes are preferably formed and iso-aldehydes only to a lesser degree. Finally, the possible side-reaction, the hydrogenation of olefins to saturated hydrocarbons, is also appreciably lower than when cobalt catalysts are employed.

In the industrially established processes, modified hydridorhodium carbonyls are employed as rhodium catalysts; i.e. compounds which, apart from rhodium, hydrogen and carbon monoxide, also contain at least one other ligand. Such ligands are organic compounds of an element of Group VA of the Periodic Table as well as esters, e.g. of phosphorous or arsenous acid. Tertiary phosphines or phosphites have proved to be particularly suitable. Normally they are used in excess and then form part of the reaction medium.

Of the hydroformylation processes which work with modified hydridorhodium carbonyls as catalysts, the process described in the DE-PS No. 26 27 354 exhibits one special feature. The reaction of the olefin, carbon monoxide and hydrogen takes place in the liquid phase in the presence of water and water-soluble rhodium complex compounds. The solubility of the rhodium complex compounds is achieved by the use of sulfonated triarylphosphines as complex components. This procedure has a number of remarkable advantages. In particular, it permits a very simple separation of the reaction product and the catalyst and ensures near complete recovery of the rhodium. The catalyst is removed from the reaction product simply by separation of the aqueous and organic phases; i.e. without distillation and thus without thermal loading of the aldehydes and alcohols formed. Owing to the extremely low solubility of the catalyst in aldehyde and alcohol, hardly any valuable metal is removed with the reaction product.

The catalyst system is either prepared separately and then introduced into the reaction zone or formed in situ. The first route requires special apparatus to react the starting rhodium or rhodium compounds, water-soluble phosphine, carbon monoxide, and hydrogen. Furthermore, the aqueous solution of the reaction product must be transferred into the reactor. Therefore, the second route is preferred; i.e. the in situ preparation of the catalyst system in the hydroformylation reactor.

Here the starting substances are rhodium, rhodium oxide, or an inorganic rhodium salt, the water-soluble phosphine, and water as a solvent, and the mixture is treated with carbon monoxide and hydrogen at temperatures and pressures customary for the hydroformylation reaction. A disadvantage of this process is that rhodium and rhodium oxides react only with difficulty, due to their insolubility in water, and the water-soluble, inorganic rhodium salts such as rhodium chloride or rhodium sulfate have a corrosive effect and therefore can only be used in exceptional cases. Instead of water-soluble rhodium salts, salts can also be used which are soluble in organic solvents. Then, however, rhodium losses must be expected at the beginning of the reaction leading to the formation of the catalyst system accompanying the hydroformylation reaction. Rhodium is removed from the reactor together with the aldehyde formed as long as there is still valuable metal present in the organic solvent.

Therefore, the problem consisted of the need to develop a process which makes it possible to preform the catalyst system consisting of a rhodium complex compound and water soluble phosphine in the hydroformylation reactor, without the disadvantages of corrosion or loss of valuable metal or disproportionately long reaction periods.

The invention consists in a process for the preparation of aldehydes by the reaction of olefinically unsaturated compounds with carbon monoxide and hydrogen at temperatures of 20° to 150° C. and pressures of 0.1 to 20 MPa in the liquid phase in the presence of water and a water soluble rhodium-containing complex compound as a catalyst. It is characterized in that, before commencement of the hydroformylation reaction, the rhodium complex compound is preformed from the rhodium salt of a carboxylic acid with 2 to 18 carbon atoms dissolved in an aliphatic, cycloaliphatic or aromatic hydrocarbon by reaction with carbon monoxide and hydrogen at pressures of 0.1 to 1.8 MPa and temperatures of 50° to 100° C. The reaction takes place in the presence of an aqueous solution of a water-soluble triarylphosphine or the aqueous solution is added after the reaction of the previously prepared rhodium complex compound.

Surprisingly, it has been shown that the active catalyst system is formed within a few hours when the reaction conditions according to the invention are observed. Although the central atom and ligands are present in various phases of a heterogeneous two-phase system, the reduction of the rhodium and its transition from the organic phase to the aqueous phase takes place rapidly.

The carbon monoxide/hydrogen mixture, and particularly the water soluble arylphosphines dissolved in the aqueous phase, act as reduction agents on the rhodium. They are oxidized to compounds of pentavalent phosphorus which do not form any catalytically active complex compound with rhodium and are lost as ligands. Therefore, it is better not to add the aqueous solution of the substituted arylphosphine to the organic phase until after the reaction of the rhodium salt with carbon monoxide and hydrogen has been completed.

The starting substances for the preparation of the catalyst system are the rhodium salts of organic acids containing 2 to 18 carbon atoms. The acids can be monobasic or polybasic, straight-chain or branched. Salts of saturated or unsaturated aliphatic acids and salts of aromatic acids are all suitable. The salts are prepared, for example, by the reaction of aqueous rhodium salt solutions, such as rhodium (III) nitrate or rhodium (III) sulfate with aqueous solutions of salts of the organic acids or by the reaction of rhodium oxide or rhodium oxide hydrates with the free acids.

The rhodium salts of saturated monocarboxylic acids with 2 to 10 carbon atoms are particularly suitable for use in the process according to the invention. Examples of these acids are acetic acid, propionic acid, n-butyric acid, i-butyric acid, pentanoic acid, hexanoic acid, and 2-ethylhexanoic acid. Special cleaning steps subsequent to the preparation of the salts are generally not required. In most cases, the reaction product can be taken up directly in the organic solvent in which the reaction with carbon monoxide and hydrogen subsequently takes place.

Aliphatic, cycloaliphatic or aromatic hydrocarbons are used as organic solvents. No special demands are placed on the physical properties of the hydrocarbons. Of course, they must be free of any contaminants which could deactivate the catalytically active rhodium. The concentration of the rhodium in the hydrocarbon is not critical, but it is advisable to employ moderately concentrated solutions, in particular, those containing at least 3000 mg rhodium per liter of solution. It is not necessary to employ uniform hydrocarbons, as mixtures thereof are also suitable as solvents for the rhodium salts. Pentane, hexane, gasoline fractions of crude oil, toluene and xylenes have proven their worth for this purpose.

The rhodium salt dissolved in hydrocarbon is treated with carbon monoxide and hydrogen in order to convert it into the catalytically active form. The composition of the $CO/H_2$ mixture can be varied within a wide range; it is possible to use both mixtures rich in carbon monoxide and those rich in hydrogen. Normally, mixtures are employed which contain carbon monoxide and hydrogen in a ratio of approximately 1:1; i.e. mixtures which exhibit a composition similar to the one also used in the subsequent hydroformylation. The rhodium salts are reacted at 50° to 100° C. and pressures of 0.1 to 1.8 MPa. It has been found that 60° to 90° C. and 0.2 to 0.5 MPa are preferred; these are conditions which ensure an optimum course of the reaction. A rhodium hydridocarbonyl is formed as the reaction product. According to its solubility, the primarily formed rhodium carbonyl compound passes into the aqueous solution of the water soluble triarylphosphine and is converted there into the rhodium phosphine complex compound.

The term water soluble triarylphosphines includes compounds which are soluble in water owing to the presence of one or several sulfonate or carboxylate groups. They have the general formula:

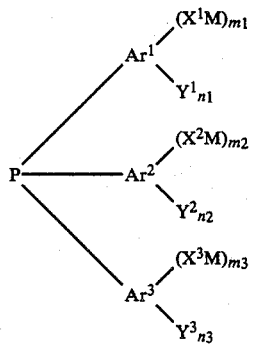

In this formula, $Ar^1$, $Ar^2$, $Ar^3$ each denote a phenyl or naphthyl group; $Y^1$, $Y^2$, $Y^3$ are each a straight or branched chain alkyl group with 1 to 4 carbon atoms, an alkoxy group, a halogen atom, OH, CN, $NO_2$, or $R^1R^2N$, wherein $R^1$ and $R^2$ each are a straight or branched chain alkyl group with 1 to 4 carbon atoms; $X^1$, $X^2$, $X^3$ are individually a carboxylate (COO—) group or a sulfonate ($SO_3-$) group; $m_1$, $m_2$, $m_3$ are individually whole numbers from 0 to 3, at least one of $m_1$, $m_2$, or $m_3$ being equal to or greater than 1; and $n_1$, $n_2$, $n_3$ are individually whole numbers from 0 to 5. M is an alkali metal ion, an equivalent of an alkaline earth metal ion or zinc ion, an ammonium or quaternary ammonium ion with the general formula $N(R^3R^4R^5R^6)+$, where $R^3$, $R^4$, $R^5$, $R^6$ are each a straight or branched chain alkyl group with up to 18 carbon atoms. Quaternary ammonium groups wherein three of the groups $R^3$, $R^4$, $R^5$, $R^6$ contain 1 to 4 carbon atoms and the fourth group 1 to 18 carbon atoms have been found particularly useful.

Preferred water soluble triarylphosphines are those in which $Ar^1$, $Ar^2$, $Ar^3$ each denote a phenyl group and $X^1$, $X^2$, $X^3$ each stand for a sulfonate group or a carboxylate group. Examples of such compounds are triphenylphosphine-tri-sodium-trisulfonate, triphenylphosphine-tri(tetraalkylammonium)trisulfonate, triphenylphosphine-tri-sodium-tricarboxylate.

The sulfonated or carboxylated arylphosphines can be used individually or as mixtures containing varying numbers of sulfonic acid groups or carboxylate groups; e.g. mixtures of triarylphosphine trisulfonic acids and triarylphosphine disulfonic acids. Moreover, the sulfonats and carboxylates do not have to contain the same cation. Mixtures of salts which can be derived from various metals and/or contain ammonium ions and/or quaternary alkylammonium ions are also suitable.

It is advisable to adjust the concentration of the water-soluble triarylphosphines in the aqueous solution to the value which is necessary for the subsqunt hydroformulation; i.e. to about 25 to 30% by weight based on the solution.

As already explained above, the phosphine solution can be added to the aqueous rhodium salt solution. In order to avoid phosphine loses, it is often advisable to prepare the rhodium-carbonyl compound first and then to add the phosphine solution.

The course of the reaction between phosphine and rhodium can be determined from the reduction of the rhodium concentration in the organic phase. Generally, the reaction has been completed after five to eight hours after which rhodium is no longer detectable in the organic phase. As soon as this condition has been reached, the reaction conditions required for the hydroformylation reaction can be set; i.e. temperatures of 20° to 150° C. and pressures of 0.1 to 20 MPa, and olefin added to the reactor.

The organic solvent remaining in the reactor after the preforming phase is removed from the reaction system together with the aldehyde formed at the beginning of the reaction between olefin and synthesis gas and separated during the work-up of the reaction product.

The process according to the invention is suitable quite generally for the hydroformylation of olefinically unsaturated compounds. It has proved particularly suitable for the reaction of olefins with 2 to 12 carbon atoms. These olefins can be linear or branched and exhibit a terminal or internal double bond. Examples of such olefins are: ethylene, propylene, 1-butene, 2-butene, 1-pentene, 2-methyl-1-butene, 4,4-dimethyl-1-nonene, and 1-dodecene. Linear olefins with 2 to 8 carbon atoms such as ethylene, propylene, 1-butene, 1-pentene, 1-hexene, 1-heptene and 1-octene are preferred.

The aqueous catalyst solution contains the water soluble phosphines in a concentration of 25 to 30% by weight, preferably 26 to 28% by weight and rhodium in a concentration of 450 to 800 ppm by weight, preferably 500 to 600 ppm, each based on the aqueous solution. The total pressure of hydrogen and carbon monoxide is 1 to 200 bar (100 to $2\times10^4$ kPa), preferably 10 to 100 bar ($1\times10^3$ to $1\times10^4$ kPa). The composition of the synthesis gas, i.e. the ratio of carbon monoxide to hydrogen can be varied within a wide range. Generally, synthesis gas is employed where the volume ratio of carbon monoxide to hydrogen is 1:1 or only deviates slightly from this figure. The reaction takes place at temperatures from 20° to 150° C. and can be carried out both continuously or batchwise.

EXAMPLE 1

In an autoclave, solutions of triphenylphosphine trisulfonate in water (about 30% by weight salt, based on the solution) and rhodium-2-ethylhexanoate in toluene (rhodium content about 10 g/l) are treated with synthesis gas (CO:$H_2$=1:1) while stirring at about 80° C. and a pressure of 0.4 MPa. The transition of the rhodium dissolved as a salt in toluene is checked by regular analysis of the organic solvent. After about 5 hours, rhodium is no longer detectable in the organic phase and the rhodium content in the aqueous phase then corresponds to the rhodium originally used.

EXAMPLE 2

In an autoclave a solution of rhodium hexanoate in toluene (rhodium content 5 g/l) is treated with synthesis gas (CO:$H_2$=1:1) while stirring at 70° C. and a pressure of 0.7 MPa. After 3 hours, just an amount of a solution of triphenylphosphine trisulfonate in water (about 28% by weight salt, based on the solution) is added to the solution of the rhodium compound so that a P (III): Rh ratio of approximately 100:1 results. The mixture is stirred for another hour. Analysis shows that all the rhodium has gone from the organic to the aqueous phase.

Although only a limited number of specific embodiments of the present invention have been expressly disclosed, it is, nonetheless, to be broadly construed, and not to be limited except by the character of the claims appended hereto.

What we claim is:

1. A process for the preparation of a rhodium catalyst for use in a hydroformylation reaction comprising dissolving a carboxylic acid salt of rhodium in a solvent taken from the class consisting of aliphatic, cycloaliphatic, aromatic hydrocarbons, and mixtures thereof to form an organic phase, said carboxylic acid having 2 to 18 carbon atoms, reacting said salt with carbon monoxide and hydrogen at a pressure of 0.1 to 1.8 MPa and a temperature of 50° to 100° C. to form a rhodium hydridocarbonyl, reacting said hydridocarbonyl with an aqueous solution of a triarylphosphine.

2. The process of claim 1 wherein said aqueous solution of said triarylphosphine is present during the reaction of said salt with said carbon monoxide and said hydrogen.

3. The process of claim 1 wherein said aqueous solution of said triarylphosphine is added after the reaction of said salt with said carbon monoxide and said hydrogen.

4. The process of claim 1 wherein said carboxylic acid has 2 to 10 carbon atoms and is saturated.

5. The process of claim 1 wherein said salt is rhodium (III)-2-ethylhexanoate.

6. The process of claim 1 wherein said solvent is taken from the class consisting of pentane, hexane, gasoline, toluene, and xylene.

7. The process of claim 1 wherein the concentration of rhodium in said organic phase is at least 3000 mg/liter.

8. The process of claim 1 wherein said pressure is 0.2 to 0.5 MPa and said temperature is 60° to 90° C.

9. The process of claim 1 wherein said triarylphosphine is of the formula

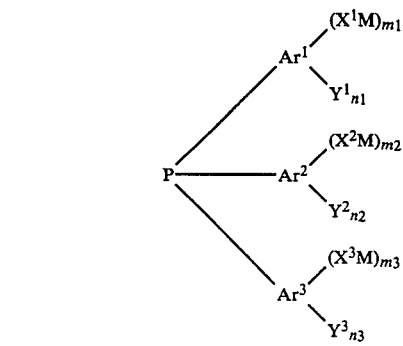

wherein $Ar^1$, $Ar^2$, and $Ar^3$ individually denote phenyl or naphthyl; $Y^1$, $Y^2$, and $Y^3$ individually represent straight or branched chain alkyl groups each having 1 to 4 carbon atoms, alkoxy, halogen, OH, CN, $NO_2$, or $R'R^2N$, wherein R and $R^2$ are each a straight or branched chain alkyl group having 1 to 4 carbon atoms; $X^1$, $X^2$, and $X^3$ individually being a carboxylate or sulfonate group, $m_1$, $m_2$, and $m_3$ individually being integers from 0 to 3, at least one of $m_1$, $m_2$, and $m_3$ not being 0; $n_1$, $n_2$, and $n_3$ individually being integers from 0 to 5; and M representing an alkali metal ion, an alkaline earth metal or zinc ion, an ammonium or quaternary ammonium ion of the formula $N(R^3R^4R^5R^6)^+$, wherein $R^3$, $R^4$, $R^5$, and $R^6$ are individually straight or branched chain alkyls each having up to 18 carbon atoms.

10. The process of claim 9 wherein $R^3$, $R^4$, and $R^5$ are each straight or branched chain alkyls having 1 to 4 carbon atoms and $R^6$ is a straight or branched chain alkyl having 1 to 18 carbon atoms.

* * * * *